US006689805B2

(12) United States Patent
Cho et al.

(10) Patent No.: US 6,689,805 B2
(45) Date of Patent: Feb. 10, 2004

(54) PYRAZOLE-3-ONE DERIVATIVE, METHOD FOR PREPARING THE SAME, AND PHARMACEUTICAL COMPOSITION CONTAINING THE SAME

(75) Inventors: Il Hwan Cho, Seoul (KR); Ji Young Noh, Busan (KR); Sang Wook Park, Suwon (KR); Hyung Chul Ryu, Yongin (KR); Jee Woong Lim, Gunpo (KR); Jong Hoon Kim, Anyang (KR); Myeong Yun Chae, Seongnam (KR); Dal Hyun Kim, Suwon (KR); Sung Hak Jung, Seoul (KR); Hyun Jung Park, Jeonrabuk-do (KR); Young Hoon Kim, Seoul (KR); In Ki Min, Yongin (KR)

(73) Assignee: CJ Corp. (KR)

( * ) Notice: Subject to any disclaimer, the term of this patent is extended or adjusted under 35 U.S.C. 154(b) by 0 days.

(21) Appl. No.: 10/461,978

(22) Filed: Jun. 13, 2003

(65) Prior Publication Data

US 2004/0002532 A1 Jan. 1, 2004

(30) Foreign Application Priority Data

Jun. 24, 2002 (KR) .................................. 10-2002-35411

(51) Int. Cl.$^7$ ..................... A61K 31/4152; A61P 35/00; C07D 231/20; C07D 231/24
(52) U.S. Cl. ................... 514/404; 548/366.1; 548/371.1
(58) Field of Search ........................... 548/366.1, 371.1; 514/404

(56) References Cited

U.S. PATENT DOCUMENTS

| 5,466,823 A | 11/1995 | Talley et al. |
| 5,633,272 A | 5/1997 | Talley et al. |

FOREIGN PATENT DOCUMENTS

| WO | 95/00501 | 1/1995 |

OTHER PUBLICATIONS

"Current Perspective Recent advances in the management of colorectal cancer"; Authors: E.V. Cutsem, M. Dicato, J. Wils; European Journal of Cancer 37; Elsevier Science Ltd.; 2001; pp. 2302–2309.
Monthly Focus: Central & Peripheral Nervous Systems; "Anti–inflammatory drugs: a hope for Alzheimer's disease?"; Authors: Michael Hull, Klaus Lieb & Bernd L. Fiebich; Asley Publications Ltd.; 2000; pp. 671–683.
News and Views; "Towards a better aspirin"; Author: John Vane; Nature, vol. 367; Jan. 20, 1994; pp. 215–216.

Meeting Report; "COX–1 and COX–2: Toward the Development of More Selective NSAIDs"; Authors: Bruno Battistini, Regina Botting and Y.S. Bakhle; DN & P 7 (8); Oct. 1994; pp. 501–512.
Chapter 19; "Selective Cycloozygenase Inhibitors"; Authors: David B. Reitz and Karen Seibert; Annual Reports in Medicinal Chemistry–30; Academic Press, Inc.; 1995; pp. 179–188.
Pergamon; "Synthesis and Biological Evaluation of 2, 3–Diarylthiophenes as Selective COX–2 and COX–1 Inhibitors"; Authors: Yves Leblanc, Jacques Yves Gauthier, Diane Ethier, Jocelyne Guay, Joseph Mancini, Denis Riendeau, Philip Tagari, Philip Vichers, Elizabeth Wong and Petpiboon Prasit; Bioorganic & Medicinal Chemistry Letters, vol. 5, No. 18; Elsevier Science Ltd.; 1995; pp. 2123–2128.
"Synthesis and Biological Evaluation of the 1, 5–Diarylpyrazole Class of Cycloozygenase–2 Inhibitors: Indentification of 4–[5–(4–Methylphenyl)–3–(trifluoromethyl)–1H–pyrazol–1–yl] benzenesulfonamide (SC–58635, Celeoxib)"; Authors: Thomas D.Penning, et al.; Journal of Medicinal Chemistry vol. 40, No. 9; American Chemical Society; 1997; pp. 1347–1365.

Primary Examiner—Robert W. Ramsuer
(74) Attorney, Agent, or Firm—Cantor Colburn LLP

(57) ABSTRACT

A pyrazole-3-one derivative of formula 1 or a non-toxic salt thereof, a preparation method thereof, and a pharmaceutical composition containing the derivative or the salt as an active ingredient are provided:

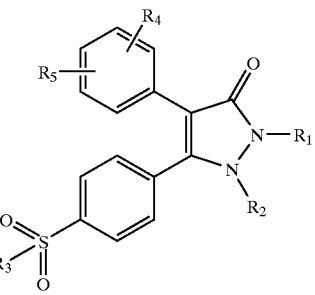

Formula 1 wherein:
$R_1$ and $R_2$ each independently represent $C_1$–$C_3$ alkyl, aryl, or substituted aryl;
$R_3$ represents amino or methyl;
$R_4$ and $R_5$ each independently represent hydrogen, $C_1$–$C_3$ alkyl, halogen, methyl substituted with halogen, $C_1$–$C_3$ alkoxy, cyano, or nitro;
or a non-toxic salt thereof.

14 Claims, No Drawings

PYRAZOLE-3-ONE DERIVATIVE, METHOD FOR PREPARING THE SAME, AND PHARMACEUTICAL COMPOSITION CONTAINING THE SAME

This U.S. non-provisional application claims priority under 35 U.S.C. §119 to Korean Patent Application No. 2002-35411, filed on Jun. 2002, in the Korean Intellectual Property Office, the contents of which are incorporated herein by reference in its entirety.

BACKGROUND OF THE INVENTION

1. Field of the Invention

The present invention relates to a pyrazole-3-one derivative or a n-toxic salt thereof, a method for preparing the same, and a pharmaceutical composition containing the same as an active ingredient.

2. Description of the Related Art

Most nonsteroidal antiinflammatory agents are responsible for locking enzyme, cyclooxygenase (COX) or prostaglandin G/H synthase, o reduce inflammation, pain, or fever. In addition, they inhibit uterus contraction caused by hormones and also inhibit growth of several cancers. Cyclooxygenase-1 (COX-1) was first discovered in bovine. The COX-1 is constitutively expressed in a variety of cell types. Unlike the COX-1, cyclooxygenase-2 (COX-2) is a recently discovered isoform of cyclooxygenase that can be easily induced by mitogen, endotoxin, hormone, growth factor, or cytokine.

Prostaglandin is a potent mediator for various pathological and physiological processes. The COX-1 plays important physiological roles such as in the release of endogenous prostaglandin, the maintenance of the shape and the function of stomach, and the blood circulation in the kidney. On the other hand, the COX-2 is induced by an inflammatory factor, hormone, a growth factor, or cytokine. Therefore, the COX-2 is involved in pathological processes of prostaglandin, unlike the constitutive COX-1. In this regard, selective inhibitors of the COX-2 produce fewer and less side effects in terms of action mechanism in comparison with conventional nonsteroidal antiinflammatory agents. In addition, they reduce inflammation, pain, and fever and inhibit uterus contraction caused by hormones and growth of several cancers. In particular, they are effective in decreasing side effects such as stomach toxicity and kidney toxicity. Still furthermore, they inhibit the synthesis of contractile prostanoid, thereby leading to suppression of the contraction of smooth muscles. Therefore, they help in preventing premature birth, menstrual irregularity, asthma, and eosinophilic disease.

Recently, it was reported that nonsteroidal antiinflammatory agents are effective in treating large intestine cancer [*European Journal of Cancer*, Vol 37, p2302, 2001], prostate cancer [*Urology*, Vol 58, p127, 2001], and dementia [*Exp. Opin. Invest. Drugs*, Vol 9, p671, 2000].

In addition, it is anticipated that selective inhibitors of the COX-2 would be effective in treating osteoporosis and glaucoma. Utility of selective inhibitors of the COX-2 is well described in publications [John Vane, "Towards a Better Aspirin" in *Nature*, Vol.367, pp215–216, 1994; Bruno Battistini, Regina Botting and Y. S. Bakhle, "COX-1 and COX-2: Toward the Development of More Selective NSAIDs" in *Drug News and Perspectives*, Vol.7, pp501–512, 1994; David B. Reitz and Karen Seibert, "Selective Cyclooxygenase Inhibitors" in *Annual Reports in Medicinal Chemistry*, James A. Bristol, Editor, Vol. 30, pp179–188, 1995].

Various selective COX-2 inhibitors having different structures are known. Among them, a selective COX-2 inhibitor having a diaryl heterocyclic structure, i.e. a tricyclic structure has been widely studied as a potent candidate. The diaryl heterocyclic structure has a central ring and a sulfonamide or methylsulfone group attached to one of the aryl rings. An initial substance having such diaryl heterocyclic structure is Dup697 [*Bioorganic & Medicinal Chemistry Letters*, Vol 5, p2123, 1995]. Since then, SC-58635 having a pyrazol ring (*Journal of Medicinal Chemistry*, Vol 40, p1347, 1997) and MK-966 having a furanone ring (WO 95/00501) were discovered as derivatives of the Dup697.

One selective COX-2 inhibitor, Celecoxib of formula 14 is disclosed in U.S. Pat. No. 5,466,823. The Celecoxib is a substituted pyrazolyl benzenesulfonamide derivative.

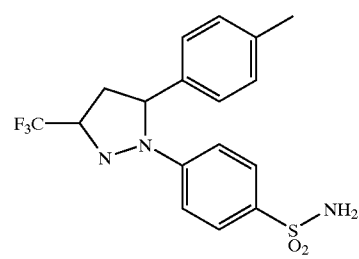

Formula 14

Another selective COX-2 inhibitor, Rofecoxib of formula 15 is disclosed in WO 95/00501. The Rofecoxib has a diaryl heterocyclic structure with a central furanone ring.

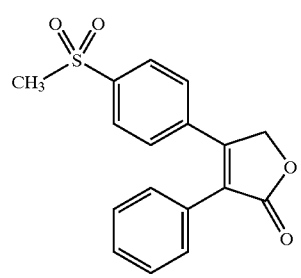

Formula 15

Valdecoxib of formula 16 as another selective COX-2 inhibitor is disclosed in U.S. Pat. No. 5,633,272. The Valdecoxib has a phenylsulfonamide moiety with a central isoxazole ring.

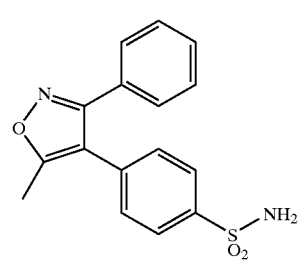

Formula 16

The selective COX-2 inhibitors of formulas 14 to 16 are effective inflammatory therapeutic agents with fewer and less side effects in comparison with conventional nonsteroidal antiinflammatory agents.

SUMMARY OF THE INVENTION

An aspect of the present invention provides a pyrazole-3-one derivative of formula 1 or a non-toxic salt thereof.

Another aspect of the present invention provides a method for preparing a pyrazole-3-one derivative or a non-toxic salt thereof.

Another aspect of the present invention provides a pharmaceutical composition comprising a pyrazole-3-one derivative or a non-toxic salt thereof as an active ingredient for the treatment of fever, pain, and inflammation.

Yet another aspect of the present invention provides a pharmaceutical composition comprising a pyrazole-3-one derivative or a non-toxic salt thereof as an active ingredient for the treatment of cancers and dementia.

DETAILED DESCRIPTION OF THE INVENTION

According to an aspect of the present invention, there is provided a pyrazole-3-one derivative represented by formula 1:

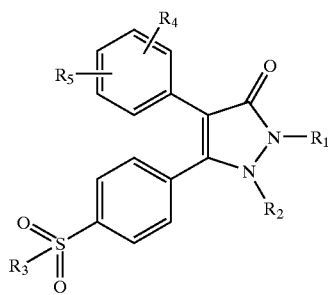

Formula 1 wherein:
$R_1$ and $R_2$ each independently represent $C_1$–$C_3$ alkyl, aryl, or substituted aryl;
$R_3$ represents amino or methyl;
$R_4$ and $R_5$ each independently represent hydrogen, $C_1$–$C_3$ alkyl, halogen, methyl substituted with halogen, $C_1$–$C_3$ alkoxy, cyano, or nitro;
or a non-toxic salt thereof.

Preferably, the $R_1$ and $R_2$ each independently represent $C_1$–$C_3$ alkyl; $R_3$ represents methyl; and $R_4$ and $R_5$ each independently represent hydrogen, $C_1$–$C_3$ alkyl, halogen, or $C_1$–$C_3$ alkoxy.

Preferably, the position of $R_4$ and $R_5$ is respectively 3- and 4-, 2- and 4-, 3- and 5-, or 3- and 2-, and more preferably 3- and 4-.

The pyrazole-3-one derivative of formula 1 may be present in a form of a non-toxic salt. The term, "non-toxic salt" as used herein refers to a pharmaceutically acceptable, toxin-free salt, including an organic salt and an inorganic salt.

The Inorganic salt of the pyrazole-3-one derivative of formula 1 includes an inorganic salt of aluminum, ammonium, calcium, copper, iron, lithium, magnesium, manganese, potassium, sodium, or zinc but is not limited thereto. Preferably, an inorganic salt of ammonium, calcium, potassium, or sodium is used.

The organic salt of the pyrazole-3-one derivative of formula 1 includes an organic amine salt of primary, secondary, or tertiary amine, substituted amine that is present in nature, or cyclic amine, or a salt of a basic ion exchange resin but is not limited thereto. Examples of the salt of a basic ion exchange resin include a salt of arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpyperidine, N-methylglucamine, glucamine, glucosamine, histidine, hydroamine, N-(2-hydroxyethyl)pyperidine, N-(2-hydroxyethyl)pyrrolidine, isopropylamine, lysine, methylglucamine, morpholine, piperazine, pyperidine, polyamine resin, procaine, purine, theobromine, triethylamine, trimethylamine, tripropylamine, and tromethamine.

The pyrazole-3-one derivative of formula 1 may be present in a form of an organic acid salt or an inorganic acid salt.

Examples of the organic acid salt or the inorganic acid salt of the pyrazole-3-one derivative of formula 1 include a salt of acetic acid, adipic acid, aspartic acid, 1,5-naphthalene disulfonic acid, benzene sulfonic acid, benzoic acid, camphor sulfonic acid, citric acid, 1,2-ethane disulfonic acid, ethane sulfonic acid, ethylenediaminetetraacetic acid, fumaric acid, glucoheptonic acid, gluconic acid, glutamic acid, hydroiodic acid, hydrobromic acid, hydrochloric acid, icethionic acid, lactic acid, maleic acid, malic acid, madelic acid, methane sulfonic acid, mucinic acid, 2-naphthalenedisulfonic acid, nitric acid, oxalic acid, pentothenic acid, phosphoric acid, pivalric acid, propionic acid, salicylic acid, stearic acid, succinic acid, sulfuric acid, tartaric acid, p-toluene sulfonic acid, undecanoic acid, and 10-undecenoic acid. Preferably, a salt of succinic acid, hydrobromic acid, hydrochloric acid, maleic acid, methanesulfonic acid, phosphoric acid, sulfuric acid, or tartaric acid is used.

The pyrazole-3-one derivative of the present invention preferably includes:
5-(4-methanesulfonylphenyl)-4-(4-methoxyphenyl)-1,2-dimethyl-1,2-dihydropyrazole-3-one;
5-(4-methanesulfonylphenyl)-1,2-dimethyl4-phenyl-1,2-dihydropyrazole-3-one;
5-(4-methanesulfonylphenyl)-1,2-dimethyl-4-(4-methylphenyl)-1,2-dihydropyrazole-3-one; and
4-(3,4-dichlorophenyl)-5-(4-methanesulfonylphenyl)-1,2-dimethyl-1,2-dihydropyrazole-3-one.

According to another aspect of the present invention, there is provided a propionic acid derivative as an intermediate for the synthesis of the pyrazole-3-one derivative of formula 1, as represented by formula 4:

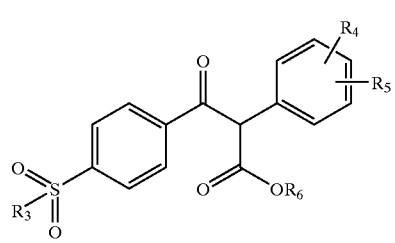

Formula 4 wherein, $R_3$, $R_4$, and $R_5$ are as defined in formula 1 and $R_6$ represents $C_1$–$C_3$ alkyl.

According to another aspect of the present invention, there is provided a method for preparing a pyrazole-3-one derivative of formula 1 or a non-toxic salt thereof, comprising reacting a hydrazine derivative of formula 5 with a propionic acid derivative of formula 4.

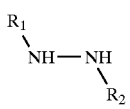

Formula 5 wherein, $R_1$ and $R_2$ are as defined in formula 1.

The aforementioned reactions are preferably carried out in a solvent which can be separated from water produced during the reaction by a Dean-Stark trap apparatus. Examples of the solvent include, but are not limited to, benzene, toluene, or xylene. More preferably, toluene is used.

The reactions are preferably carried out by heating the reactant to the boiling point of the solvent and completing the reaction. More preferably, toluene is used as a solvent and the reactants are heated to the boiling point of the tolene and refluxed to complete the reaction.

The separation and purification of the reaction products can be performed by concentration or extraction, or other processes, which is conventionally used in organic synthesis process, and optionally by a silica gel column chromatography.

The said propionic acid derivative of formula 4 may be prepared by reacting a sulfonylbenzoic acid derivative of formula 2 with a phenyl acetate derivative of formula 3 in the presence of a base.

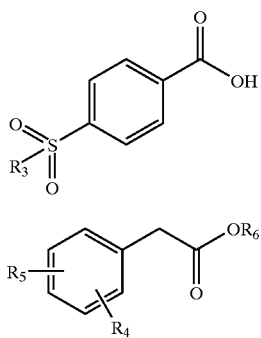

Formula 2

Formula 3 wherein, $R_3$, $R_4$, and $R_5$ are as defined in formula 1 and $R_6$ represents $C_1$–$C_3$ alkyl.

The said base includes sodium hydride, potassium carbonate, or potassium hydroxide. Preferably, sodium hydride is used.

According to another aspect of the present invention, there is provided a pharmaceutical composition comprising a therapeutically effective amount of a pyrazole-3-one derivative of formula 1 or a non-toxic salt thereof as an active ingredient and a pharmaceutically acceptable carrier for the treatment of fever, pain, and inflammation.

The pharmaceutical composition comprises a compound of formula 1 or a non-toxic salt thereof when it is a selective inhibitor of cyclooxygenase-2. Therefore, the pharmaceutical composition can be used as an antipyretic, an analgesic, and an antiinflammatory agent, with reduced side effects.

Conventional nonsteroidal antiinflammatory agents nonselectively inhibit the prostaglandin synthesis enzymes, cyclooxygenase-1 and cyclooxygenase-2. Therefore, various side effects may occur.

On the other hand, a compound of formula 1 and a non-toxic salt thereof selectively inhibit cyclooxygenase-2. Therefore, the side effects of conventional nonsteroidal antipyretics, analgesics, and antiinflammatory agents can be reduced.

The pharmaceutical composition of the present invention comprises a compound of formula 1 and/or a non-toxic salt thereof and a pharmaceutically acceptable carrier or excipient. Therefore, the pharmaceutical composition may be used as a substitute for conventional nonsteroidal antiinflammatory agents. In particular, due to the reduction of the side effects of conventional nonsteroidal antipyretics, analgesics, and antiinflammatory agents, the pharmaceutical composition of the present invention is useful for treating patients with peptic ulcer, gastritis, regional enteritis, ulcerative colitis, diverticullitis, gastrorrhagia, or hypoprothrombinemia.

The pharmaceutical composition of the present invention can be used in all inflammatory diseases associated with pathological prostaglandin and is particularly useful in treating osteoarthritis and rheumatoid arthritis which require high dosage of nonsteroidal antiinflammatory agents.

The pharmaceutical composition of the present invention can be administered in form of an adult dosage of 50 mg/kg/day to 400 mg/kg/day of the compound of formula 1. An adequate dosage is determined depending on the degree of disease severity.

According to yet another aspect of the present invention, there is provided a pharmaceutical composition comprising a therapeutically effective amount of a pyrazole-3-one derivative of formula 1 or a non-toxic salt thereof and a pharmaceutically acceptable carrier for the treatment of cancers and dementia.

Recently, it was reported that nonsteroidal antiinflammatory agents are effective in the treatment of large intestine cancer [*European Journal of Cancer*, Vol 37, p2302, 2001], prostate cancer [*Urology*, Vol 58, p127, 2001], and dementia [*Exp. Opin. Invest. Drugs*, Vol 9, p671, 2000]. Therefore, it is understood that the pharmaceutical composition of the present invention as a nonsteroidal antiinflammatory agent can also be used for the treatment of these diseases.

The pharmaceutical composition of the present invention can be administered in the form of an adult dosage of 50 mg/kg/day to 400 mg/kg/day of the compound of formula 1 or a non-toxic salt thereof. An adequate dosage is determined depending on the degree of disease severity.

The pharmaceutical composition of the present invention may be administered in the form of tablet, foam tablet, capsule, granule, powder, sustained-release tablet, sustained-release capsule (a single unit formulation or a multiple unit formulation), intravenous and intramuscular injectable solution, infusion solution, suspension, or suppository, or in other suitable dosage forms.

Sustained-release pharmaceutical dosage forms contain active ingredients with or without an initial loading dose. They are wholly or partially sustained-release pharmaceutical dosage forms to release active ingredients in a controlled manner.

Preferably, the pharmaceutical composition is orally administered.

The pharmaceutical composition further comprises a pharmaceutically acceptable excipient and/or diluent and/or adjuvant in pharmaceutically effective amounts.

Examples of the excipient and adjuvant include gellatin, a natural sugar such as sucrose and lactose, lecitin, pectin, starch such as corn starch and amylose, cyclodextrin and cyclodextrin derivative, dextran, polyvinylpyrrolidone, polyvinyl acetate, Arabic gum, arginic acid, xylose, talc, salicylic acid, calcium hydrogen phosphate, cellulose, cellulose derivative such as methylcellulose, methoxypropyl cellulose, hydroxypropylmethyl cellulose, and hydroxypropylmethylcellulose phthalate, fatty acid having 12 to 22 carbon atoms, emulsifying agent, oil and fat, in particular, vegetable glycerol ester and polyglycerol ester of saturated fatty acids, monohydric alcohol, polyhydric alcohol, polyglycol such as polyethylene glycol, aliphatic alcohol having 1 to 20 carbon atoms, or aliphatic saturated or unsaturated fatty acid ester having 2 to 22 carbon atoms with polyhydric alcohols such as glycol, glycerol, diethylene glycol, 1,2-propylene glycol, sorbitol, and mannitol.

Other suitable adjuvants include a disintegrating agent. Examples of the disintegrating agent include a cross-linked polyvinylpyrrolidone, sodium carboxymethyl starch, sodium carboxymethyl cellulose, and microcrystalline cellulose. A coating agent which is conventionally used in this field may also be used. Examples of the coating agent include acrylic acid and/or methacrylic acid and/or an ester polymer or copolymer thereof, zein, ethyl cellulose, ethyl cellulose succinate, and Shellac.

A plasticizer suitable for the coating agent is citric ester and tartaric ester, glycerol and glycerol ester, or polyethylene glycol with different chain lengths.

A liquid composition such as solution and suspension is formulated in water or a physiological acceptable organic solvent such as alcohol and aliphatic alcohol.

The liquid pharmaceutical composition may further comprise a preservative such as potassium solvate, methyl 4-hydroxybenzoate, and propyl 4-hydroxybenzoate, an antioxidant such as ascorbic acid, and a fragrant such as peppermint oil.

In addition, when the liquid pharmaceutical composition is formulated, a conventional solubilizer or emulsifier such as polyvinylpyrrolidone and polysolvate 80 may be used.

Other examples of suitable excipients and adjuvants are disclosed in Dr. H. P. Fielder, "Lexikon der Hilfsstoffe fur Pharmazie, Kosmetik und angrenzende Gebiete" [Encyclopaedia of auxiliaries for pharmacy, cosmetics and related fields].

Hereinafter, the present invention will be described more specifically by examples. However, the following examples are provided only for illustration and thus the present invention is not limited to or by them.

EXAMPLE 1

3-(4-methanesulfonylphenyl)-2-(4-methoxyphenyl)-3-oxo-propionic acid ethyl ester

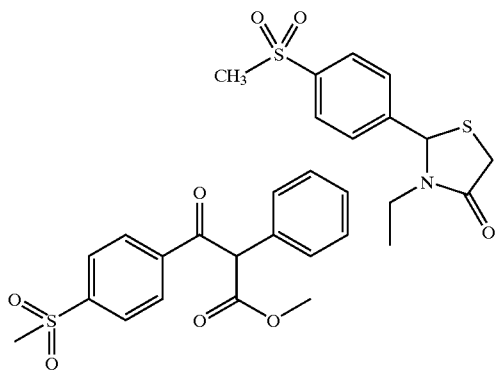

Formula 6

1 g of 4-methanesulfony benzoicacid, 970 mg of 4-methoxyphenylacetic acid ethyl ester, and 950 mg of carbonyidiimidazole were dissoved in 15 ml of dimethylformamide and 230 mg of sodium hydride were added dropwise to the solution and the mixture was reacted in room temperature for 12 hours. Afterwards, water was added to diute the resultant, followed by extraction with ethyl acetate. The obtained organic layer was dried over anhydrous magnesium sulfate to give 1.5 g of the title compound as a light yellow liquid(yield 83%).

$^1$H-NMR(400 MHz, CDCl$_3$) δ8.14(d, 2H, J=8.8 Hz), 8.04(d, 2H, J=8.8 Hz), 6.95(d, 2H, J=8.8 Hz), 6.65(d, 2H, J=8.8 Hz), 5.11(s, 1H), 4.12(q, 2H), 3.74(s, 3H), 3.10(s, 3H), 1.30(t, 3H)

1.3 g (yield 80%) of the title compound as a liquid was prepared in the same manner as in Example 1 except using 750 mg of 4-methoxyphenylacetic acid methyl ester instead of 4-methoxyphenylacetic acid ethyl ester.

$^1$H-NMR(400 MHz, CDCl$_3$) δ8.14(d, 2H, J=8.8 Hz), 8.04(d, 2H, J=8.8 Hz), 7.14(m, 5H), 5.11(s, 1H), 3.63(s, 3H), 3.09(s, 3H)

EXAMPLE 3

3-(4-methanesulfonylphenyl)-3-oxo-2-(4-methylphenyl) propionic acid ethyl ester

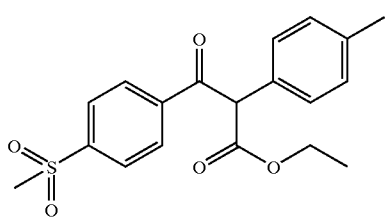

Formula 8

1.5 g (yield 83%) of the title compound as a liquid was prepared in the same manner as in Example 1 except using 0.89 mg of 4-methylphenylacetic acid ethyl ester instead of 4-methoxyphenylacetic acid ethyl ester.

$^1$H-NMR(400 MHz, CDCl$_3$) δ8.14(d, 2H, J=8.8 Hz), 8.04(d, 2H, J=8.8 Hz), 6.94(d, 2H, J=8.8 Hz), 6.64(d, 2H, J=8.8 Hz), 5.11(s, 1H), 4.13(q, 2H), 3.10(s, 3H), 2.35(s, 3H), 1.30(t, 3H)

EXAMPLE 4

2-(3,4-dichlorophenyl)-3-(4-methanesulfonylphenyl)-3-oxo-propion aicd ethyl ester

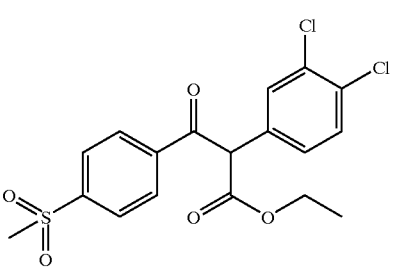

Formula 9

1.7 g (yield 85%) of the title compound as a liquid was prepared in the same manner as in Example 1 except using 1.1 g of (3,4-dichlorophenyl)acetic acid ethyl ester instead of 4-methoxyphenylacetic acid ethyl ester.

$^1$H-NMR(400 MHz, CDCl$_3$) δ8.14(d, 2H, J=8.8 Hz), 8.04(d, 2H, J=8.8 Hz), 7.09(d, 1H, J=8.4 Hz), 7.01(s, 1H), 6.88(d, 1H, J=8.4 Hz), 5.11(s, 1H), 4.13(q, 2H), 3.10(s, 3H), 1.30(t, 3H)

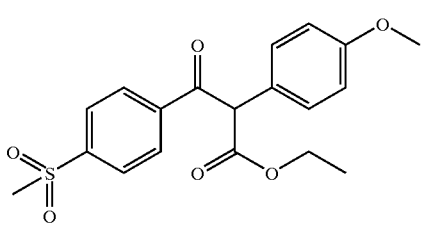

EXAMPLE 5

5-(4-methanesulfonylphenyl)-4-(4-methoxyphenyl)-1,2-dimethyl-1,2-dihydropyrazole-3-one

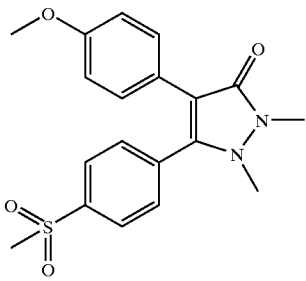

Formula 10

3-(4-methanesulfonylphenyl)-2-(4-methoxyphenyl)-3-oxo-propionic acid ethyl ester was dissoved in 20 ml of toluene and then 0.24 g of dimethyl hydrazine was added to the solution. The apparatus containing the mixture was heated and refluxed at 120° C. for 24 hours in the Dean-Stark trap apparatus. The reaction mixture was cooled, diluted with water, and extracted with ethyl acetate. The obtained organic layer was dried on anhydrous magnesium sulfate and concentrated under reduced pressure. The resultant was recrystalized with n-hexane to give 160 mg of the title compound as a yellow solid(yield 53%).

$^1$H-NMR(400 MHz, CDCl$_3$) δ8.02(d, 2H, J=8.0 Hz), 7.59(d, 2H, J=8.0 Hz), 7.26(d, 2H, J=8.0 Hz), 6.83(d, 2H, J=8.0 Hz), 3.81(s, 3H), 3.51(s, 3H), 3.15(s, 3H), 3.06(s, 3H)

FAB Mass(M+1):373

IR: (υC=O) 1637 cm$^{-1}$

Melting point: 245–247° C.

EXAMPLE 6

5-(4-methanesulfonylphenyl)-1,2-dimethyl-4-phenyl-1,2-dihydropyrazole-3-one

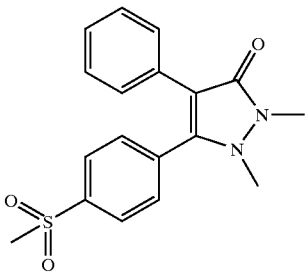

Formula 11

170 mg (yield 56%) of the title compound was prepared in the same manner as in Example 5 except using 0.3 g of 3-(4-methanesulfonylphenyl)-3-oxo-2-phenylpropionic acid methyl ester instead of 3-(4-methanesulfonylphenyl)-2-(4-methoxyphenyl)-3-oxo-propionic acid ethyl ester.

$^1$H-NMR(400 MHz, CDCl$_3$) δ7.98(d, 2H, J=8.0 Hz), 7.54(d, 2H, J=8.0 Hz), 7.28–7.19(m, 5H), 3.47(s, 3H), 3.11(s, 3H), 3.06(s, 3H)

EI Mass(M+): 342

IR: (υC=O) 1640 cm$^{-1}$

Melting point: 210–212° C.

EXAMPLE 7

5-(4-methanesulfonylphenyl)-1,2-dimethyl-4-(4-methylphenyl)-1,2-dihydropyrazole-3-one

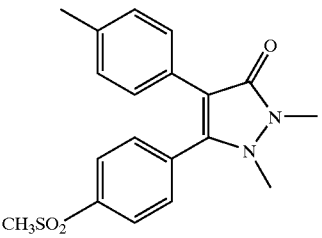

Formula 12

180 mg (yield 60%) of the title compound was prepared in the same manner as in Example 5 except using 0.3 g of 3-(4-methanesulfonylphenyl)-3-oxo-2-(4-methylphenyl)propionic acid ethyl ester instead of 3-(4-methanesulfonylphenyl)-2-(4-methoxyphenyl)-3-oxo-propionic acid ethyl ester $^1$H-NMR(400 MHz, CDCl$_3$) δ7.99(d, 2H, J=8.0 Hz), 7.55(d, 2H, J=8.00 Hz), 7.17(d, 2H, J=8.00 Hz), 7.02(d, 2H, J=8.00 Hz), 3.50(s, 3H), 3.08(s, 3H) 3.05(s, 3H), 2.29(s, 3H)

EI Mass(M+):356

IR: (υC=O) 1626 cm$^{-1}$

Melting point: 247–249° C.

EXAMPLE 8

4-(3,4-dichlorophenyl)-5-(4-methanesulfonylphenyl)-1,2-dimethyl-1,2-dihydropyrazole-3-one Formula 13

190 mg (yield 57%) of the title compound was prepared in the same manner as in Example 5 except using 0.3 g of 2-(3,4-dichlorolphenyl)-3-(4-methanesulfonylphenyl)-3-oxo-propionic acid ethyl ester instead of 3-(4-methanesulfonylphenyl)-2-(4-methoxyphenyl)-3-oxo-propionic acid ethyl ester.

$^1$H-NMR(400 MHz, CDCl$_3$) δ7.98(d, 2H, J=8.0 Hz), 7.49(d,2H,J=8.0 Hz), 7.44(d, 1H, J=8.0 Hz), 7.35(s,1H), 7.07(d, 1H, J=8.0 Hz), 3.14(s, 3H), 3.09(s, 3H), 3.08(s, 3H)

EI Mass(M+):411

IR: (υC=O) 1637 cm$^{-1}$

Melting point: 240–242° C.

Experiments

1. Evaluation of Selective COX-2 Inhibitory Activity

1) Method

In order to pharmacologically determine the selective COX-2 inhibitory activity, the percentages of the COX-1 and COX-2 inhibition of the compounds of the present invention illustrated in the Examples were measured by the following methods.

a. Assay for the COX-1 inhibitory activity using U-937

U-937 human lymphoma cells (Korean Cell Line Bank, Seoul, Korea, Accession Number: 21593) were cultured and centrifuged. The collected cells were diluted with HBSS (x1, Hank's balanced salt solution) to a concentration of $1 \times 10^6$ cells/ml. 1 ml of the dilute cell solution was placed into each well of 12-well plates. 5 μl of 1 μM solution of a test compound in DMSO and 5 μl of DMSO as a control were added to the wells. The wells were incubated in $CO_2$ incubator at 37° C. for 15 minutes. Separately, 10 mM stock solution of arachidonic acid in ethanol was diluted ten times in ethanol to prepare 1 mM solution of arachidonic acid. Arachidonic acid acts as a substrate. 10 μl of the 1 mM solution of arachidonic acid was added to each well and incubated at $CO_2$ incubator at 37° C. for 30 minutes. The cell solution of each well was placed in a centrifuge test tube and centrifuged at 10,000 rpm at 4° C. for 5 minutes. The concentration of PGE2 in the collected cells and the supernatant was quantified by means of a monoclonal kit (Cayman Chemicals). The percentages of PGE2 inhibition in a group of the test compound-treated cells in relation to a group of the DMSO-treated cells were calculated. Based on the calculated values, the COX-1 inhibitory activities were evaluated.

b. Assay for the COX-2 inhibitory activity using RAW 264.7 cell line $2 \times 10^6$ cells of RAW 264.7 cell line (Korean Cell Line Bank, Seoul, Korea, Accession Number: 40071) were inoculated into each well of 12-well plates. Each well was treated with 250 μM of aspirin and incubated at 37° C. for 2 hours. After the culture media were replaced with new culture media, the new culture media were treated with a test compound (10 nM) and incubated for 30 minutes. Then, each well was treated with interferon ɣ(100 units/ml) and lipopolysaccharide (LPS, 100 ng/ml) and incubated for 18 hours. The culture media were transferred to other test tubes. The concentration of PGE2 was quantified by means of the EIA kit (Cayman Chemicals).

2) Test Results

The test results are presented in Table 1 below. The percentages of the COX inhibition were calculated according to the following equation:

% Inhibition=(concentration of PGE2 in test compound-untreated sample−concentration of PGE2 in test compound-treated sample) / (concentration of PGE2 in test compound-untreated sample)×100

TABLE 1

| Cyclooxygenase (COX) Inhibition (%) | | |
|---|---|---|
| Samples | COX-1 (1 μM) | COX-2 (10 nM) |
| Reference (Valdecoxib) | 28.8 | 5.47 |
| Example 5 | 10.5 | 22.5 |
| Example 6 | 22.6 | 13.2 |
| Example 7 | 36.5 | 12.5 |

3) Evaluation

The in vitro test results about the percentages of the COX-1 and COX-2 inhibition are listed in Table 1.

As shown in Table 1, inhibition (%) ratios of COX-2 to COX-1 in Examples 5 to 7 were significantly higher than that in the reference, Valdecoxib. This indicates that selective inhibition of COX-2 to COX-1 of the present compound is superior to that of the reference.

The compounds of Examples 5 to 7 exhibited the COX-2 inhibitory activities significantly higher than the reference. Based on this result, it can be seen that the present compounds have reduced side effects due to enhanced selectivity and improved relief effects of fever, pain, and inflammation, compared to the reference.

As apparent from the above description, the present invention provides a pyrazole-3-one derivative or a non-toxic salt thereof, a preparation method thereof, and a pharmaceutical composition containing the derivative or the salt as an active ingredient. The pharmaceutical composition is effective in reducing fever, pain, and inflammation. In particular, as a result of reduction of the side effects of conventional nonsteroidal antiinflammatory agents, the pharmaceutical composition is useful for treating patients with peptic ulcer disease, gastritis, regional enteritis, ulcerative colitis, diverticullitis, gastrorrhagia, or hypoprothrombinemia.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A pyrazole-3-one derivative represented by formula 1:

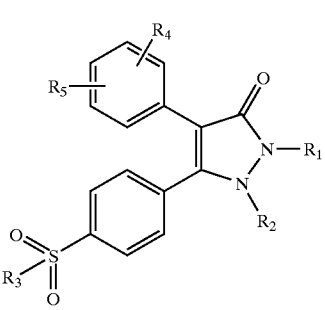

Formula 1 wherein:
$R_1$ and $R_2$ each independently represent $C_1$–$C_3$ alkyl, aryl, or substituted aryl;
$R_3$ represents amino or methyl;
$R_4$ and $R_5$ each independently represent hydrogen, $C_1$–$C_3$ alkyl, halogen, methyl substituted with halogen, $C_1$–$C_3$ alkoxy, cyano, or nitro;
or a non-toxic salt thereof.

2. The pyrazole-3-one derivative according to claim 1 wherein $R_1$ and $R_2$ each independently represent $C_1$–$C_3$ alkyl; $R_3$ represents methyl; and $R_4$ and $R_5$ each independently represent hydrogen, $C_1$–$C_3$ alkyl, halogen, or $C_1$–$C_3$ alkoxy.

3. The pyrazole-3-one derivative according to claim 1, which is selected from the group consisting of:

5-(4-methanesulfonylphenyl)-4-(4-methoxyphenyl)-1,2-dimethyl-1,2-dihydropyrazole-3-one;

5-(4-methanesulfonylphenyl)-1,2-dimethyl-4-phenyl-1,2-dihydropyrazole-3-one;

5-(4-methanesulfonylphenyl)-1,2-dimethyl-4-(4-methylphenyl)-1,2-dihydropyrazole-3-one; and 4-(3,4-dichlorophenyl)-5-(4-methanesulfonylphenyl)-1,2-dimethyl-1,2-dihydropyrazole-3-one.

4. A method for preparing a pyrazole-3-one derivative of formula 1 or a non-toxic salt thereof, comprising reacting a hydrazine derivative of formula 5 with a propionic acid derivative of formula 4:

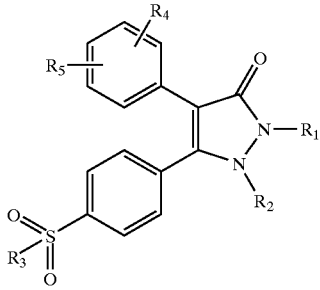

Formula 1

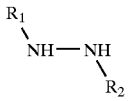

Formula 5

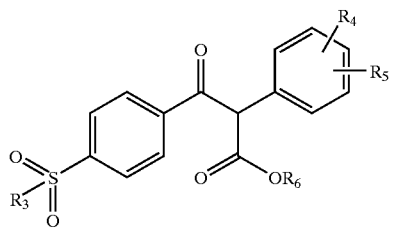

Formula 4 wherein:
- $R_1$ and $R_2$ each independently represent $C_1$–$C_3$ alkyl, aryl, or substituted aryl;
- $R_3$ represents amino or methyl;
- $R_4$ and $R_5$ each independently represent hydrogen, $C_1$–$C_3$ alkyl, halogen, methyl substituted with halogen, $C_1$–$C_3$ alkoxy, cyano, or nitro; and
- $R_6$ represents $C_1$–$C_3$ alkyl.

5. The method according to claim 4, wherein the propionic acid derivative of formula 4 is prepared by reacting a sulfonylbenzoic acid derivative of formula 2 with a phenyl acetate derivative of formula 3 in the presence of a base

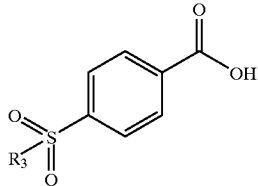

Formula 2

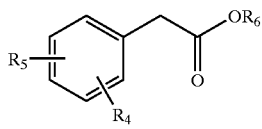

Formula 3 wherein $R_3$ represents amino or methyl;
- $R_4$ and $R_5$ each independently represent hydrogen, $C_1$–$C_3$ alkyl, halogen, methyl substituted with halogen, $C_1$–$C_3$ alkoxy, cyano, or nitro; and
- $R_6$ represents $C_1$–$C_3$ alkyl.

6. A pharmaceutical composition comprising a therapeutically effective amount of a pyrazole-3-one derivative or a non-toxic salt thereof according to claim 1 as an active ingredient and a pharmaceutically acceptable carrier for the treatment of fever, pain, and inflammation.

7. A pharmaceutical composition comprising a therapeutically effective amount of a pyrazole-3-one derivative or a non-toxic salt thereof according to claim 1 as an active ingredient and a pharmaceutically acceptable carrier for the treatment of cancers.

8. A pharmaceutical composition comprising a therapeutically effective amount of a pyrazole-3-one derivative or a non-toxic salt thereof according to claim 1 as an active ingredient and a pharmaceutically acceptable carrier for the treatment of dementia.

9. A pharmaceutical composition comprising a therapeutically effective amount of a pyrazole-3-one derivative or a non-toxic salt thereof according to claim 2 as an active ingredient and a pharmaceutically acceptable carrier for the treatment of fever, pain, and inflammation.

10. A pharmaceutical composition comprising a therapeutically effective amount of a pyrazole-3-one derivative or a non-toxic salt thereof according to claim 2 as an active ingredient and a pharmaceutically acceptable carrier for the treatment of cancers.

11. A pharmaceutical composition comprising a therapeutically effective amount of a pyrazole-3-one derivative or a non-toxic salt thereof according to claim 2 as an active ingredient and a pharmaceutically acceptable carrier for the treatment of dementia.

12. A pharmaceutical composition comprising a therapeutically effective amount of a pyrazole-3-one derivative or a non-toxic salt thereof according to claim 3 as an active ingredient and a pharmaceutically acceptable carrier for the treatment of fever, pain, and inflammation.

13. A pharmaceutical composition comprising a therapeutically effective amount of a pyrazole-3-one derivative or a non-toxic salt thereof according to claim 3 as an active ingredient and a pharmaceutically acceptable carrier for the treatment of cancers.

14. A pharmaceutical composition comprising a therapeutically effective amount of a pyrazole-3-one derivative or a non-toxic salt thereof according to claim 3 as an active ingredient and a pharmaceutically acceptable carrier for the treatment of dementia.

* * * * *